US00PP27932P2

(12) United States Plant Patent
de Bruijn

(10) Patent No.: US PP27,932 P2
(45) Date of Patent: Apr. 25, 2017

(54) ***DIERVILLA* PLANT NAMED 'DIWIBRU01'**

(50) Latin Name: *Diervilla rivularis*
Varietal Denomination: Diwibru01

(71) Applicant: William de Bruijn, Boskoop (NL)

(72) Inventor: William de Bruijn, Boskoop (NL)

( * ) Notice: Subject to any disclaimer, the term of this patent is extended or adjusted under 35 U.S.C. 154(b) by 0 days.

(21) Appl. No.: 14/757,219

(22) Filed: Dec. 7, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Diervilla rivularis*, 'Diwibru01', characterized by its bright yellow-green foliage that is maintained into fall, its yellow flowers, and its young stems that are red with sun exposure.

2 Drawing Sheets

Botanical classification: *Diervilla rivularis.*
Variety denomination: 'Diwibru01'.

CROSS REFERENCE TO A RELATED APPLICATION

This application is related to a European plant breeders' rights application filed on Dec. 11, 2014, application No. 2014/3343 and no accessibility to one of ordinary skill in the art could have been derived from printed plant breeder's rights documents. There have been no offers for sale anywhere in the world more than one year prior to the filing of this Application.

BACKGROUND OF THE INVENTION

The present invention relates to a new and distinct cultivar of *Diervilla rivularis* and will be referred to hereafter by its cultivar name, 'Diwibru01'. 'Diwibru01' is a new cultivar of bush honeysuckle grown for use as a landscape plant.

The inventor discovered the new cultivar as a naturally occurring branch mutation on an unnamed and unpatented plant of *Diervilla rivularis* that was growing in the Inventor's garden in Boskoop, The Netherlands in 2009.

Asexual reproduction of the new cultivar was first accomplished by the inventor using softwood stem cuttings in 2009 in Boskoop, The Netherlands. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Diwibru01' as a unique cultivar of *Diervilla.*

1. 'Diwibru01' exhibits bright yellow-green foliage that is maintained into fall.
2. 'Diwibru01' exhibits yellow flowers.
3. 'Diwibru01' exhibits young stems that are red with sun exposure.

The parent plant of 'Diwibru01' differs from 'Diwibru01' in having green foliage. 'Diwibru01' can be compared to *Diervilla rivularis* cultivars 'Morton' (not patented), and 'Trojan Black' (not patented). 'Morton' differs from 'Diwibru01' in having green foliage that has hues of orange and red in fall. 'Trojan Black' differs from 'Diwibru01' in having foliage that is tinted purple-bronze on the new growth and red in fall.

BRIEF DESCRIPTION OF THE DRAWINGS

The accompanying colored photographs illustrate the overall appearance and distinct characteristics of the new *Dievilla*. The photographs were taken of a one year-old plant of the new cultivar as grown outdoors in a 17-cm container in Boskoop, The Netherlands.

The photograph in FIG. 1 illustrates the overall appearance of 'Diwibru01'.

Figure 1:
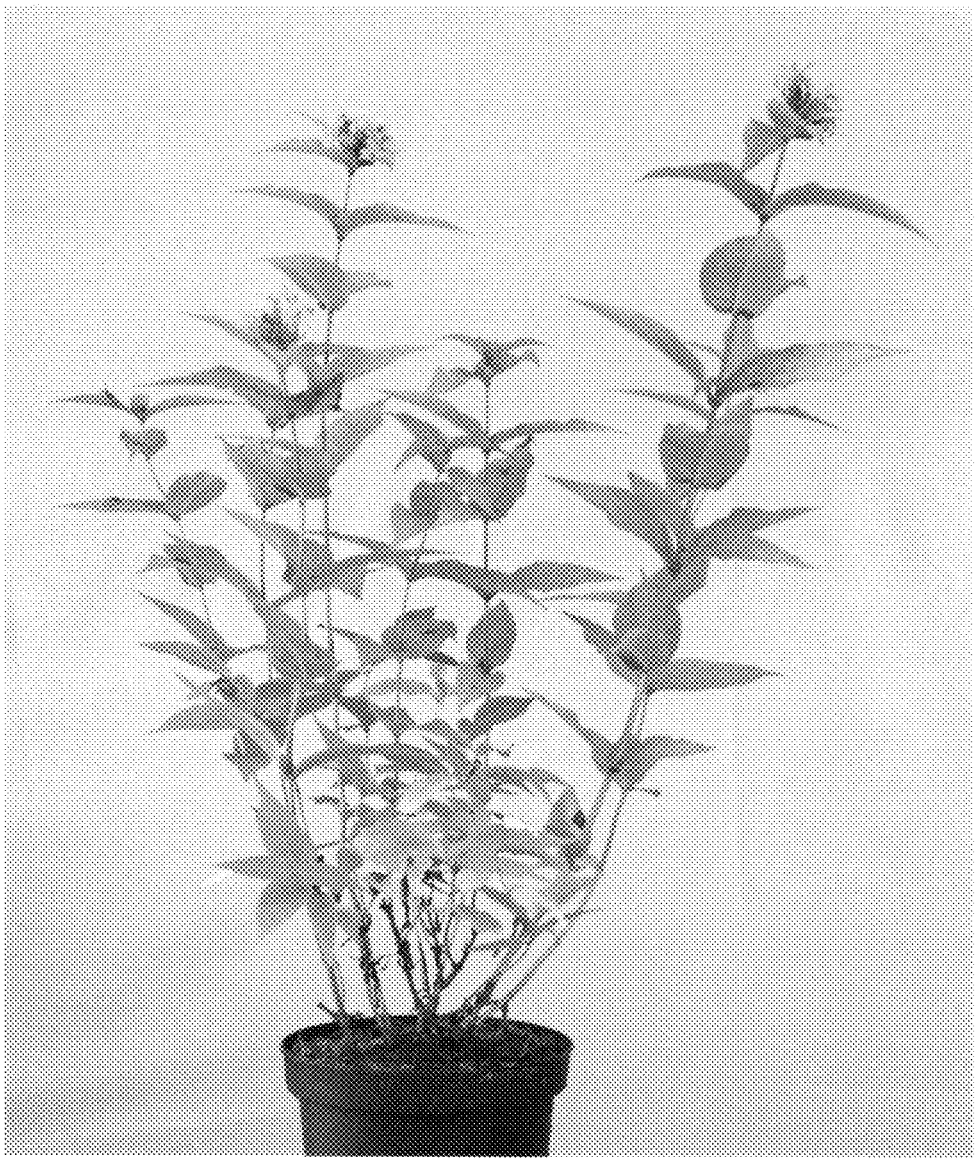
Figure 2:
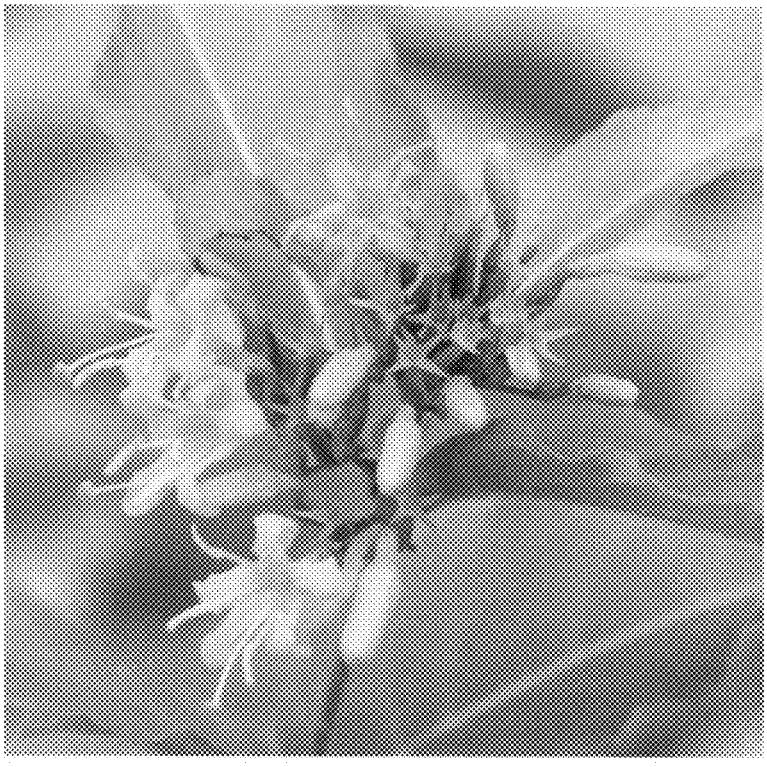

The photograph in FIG. 2 is a close-up view of an inflorescence of 'Diwibru01'.

Figure 3:
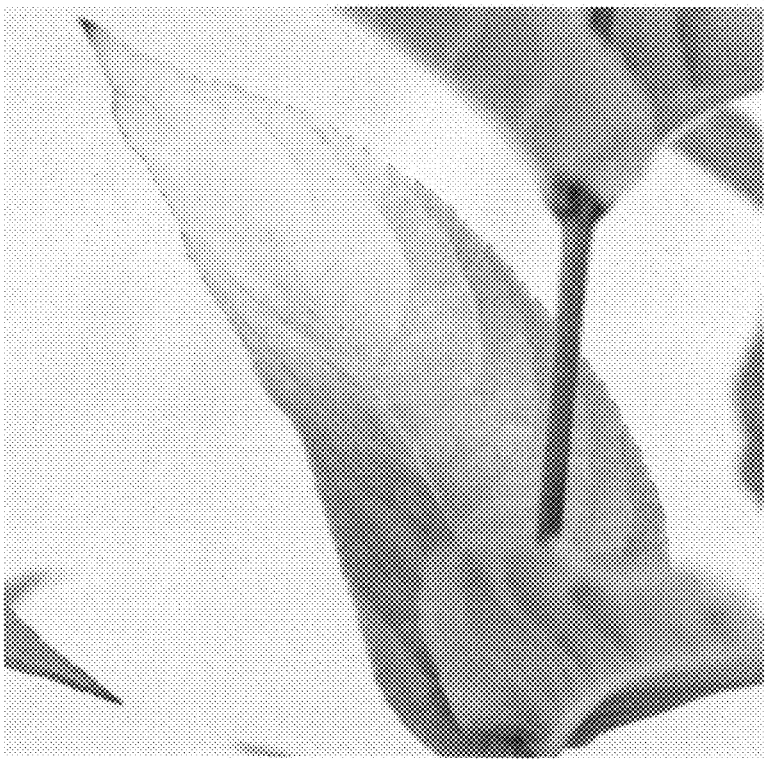

The photograph in FIG. 3 provides a close-up view of the foliage of 'Diwibru01'.

The colors in the photographs are as close as possible with the digital photography techniques available, the color values cited in the detailed botanical description accurately describe the colors of the new *Diervilla.*

DETAILED BOTANICAL DESCRIPTION

The following is a detailed description of one year-old plants of the new cultivar as grown outdoors in 17-cm containers in July in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from late spring to early summer in Boskoop, The Netherands.

*Plant habit*.—Upright.
*Plant type*.—Perennial, deciduous shrub.
*Height and spread*.—Average of 66.1 cm in height and 66 cm in width.
*Cold hardiness*.—At least in U.S.D.A. Zone 4.
*Diseases resistance*.—No particular susceptability or resistance to diseases has been oberved.
*Propagation*.—Softwood stem cuttings.
*Root description*.—Fibrous.
*Root development*.—Roots develop in 10 to 14 days in summer an fully develop as a young rooted plant in 3 months.
*Growth rate*.—Moderate.

Branch description:
*Shape*.—Rounded with two angles on oppsoite sides of beanch..
*Branch color*.—Young stems; 150C if shaded, 184A and 184B with sun exposure, mature stems; a blend of N200A to N200B.
*Branch size*.—An average of 44.7 cm in length and 3.5 cm in width.
*Stem surface*.—Slightly glossy and sparsely covered with very short hairs an average of 0.3 mm in length and too small to be measured with RHS-CC.
*Branch aspect*.—Held primarily upright.
*Branch strength*.—Very strong.
*Internode length*.—Average of 6.3 cm.
*Branching*.—An average of 16 branches emerging from base.

Foliage description:
*Leaf shape*.—Lanceolate.
*Leaf division*.—Simple.
*Leaf base*.—Truncate.
*Leaf apex*.—Apiculate.
*Leaf venation*.—Pinnate, upper veins color; N170B, lower veins color; 150D.
*Leaf margins*.—Entire.
*Leaf arrangement*.—Opposite.
*Leaf attachment*.—Sessile.
*Leaf surface*.—Upper surface; glabrous and matte, lower surface glabrous and slightly glossy, main veins on upper and lower surface moderately covered with very short hairs an average of 0.3 mm in length and too small to be measured with RHS-CC.
*Leaf size*.—Average of 11.2 cm in length and 5 cm in width.
*Leaf quantity*.—Average of 16 leaves (8 pairs) per branch.
*Leaf color*.—Young upper surface; 151A to 151B, outer margin tinged 172D, young lower surface; between 152D and 153D, mature and fall upper surface; ranging between 153C, 13A and 13B, base is N144A to N144C, mature and fall lower surface; 16B and N144D.
*Petioles*.—About 2 mm in length and 3 mm in width, upper side color 144B, lower side color 145A, surface glabrous.
*Stipules*.—Not present.

Inflorescence description:
*Inflorescence type*.—Terminal and axillary compound cymes of tubular flowers.
*Inflorescence size*.—Average of 4.8 cm in height and 6 cm in width.
*Flower fragrance*.—None.
*Lastingness of inflorescence*.—Average of one week, self-cleaning.
*Flower quantity*.—Average of 30 flowers per terminal cyme, average of 7 flowers per axillary cymes.
*Flower type*.—Single, campanulate with tubular base.
*Flower size*.—Average of 2 cm in depth and 1.3 cm in diameter.
*Flower aspect*.—Upright to outward.
*Flower buds*.—Narrow oblong in shape, color is between 150B and 151D, very base 174A to 174B, average of 1.1 cm in length and 2.5 mm in diamteter, surface is waxy.
Peduncles.—About 1.5 cm in length and 1 mm in diameter, strong, 144C in color, surface texture glabrous, round in shape.
*Pedicels*.—Up to 4 mm in length and 0.5 mm in diameter, moderately strong, 144C in color, glabrous surface, round in shape.
*Calyx*.—Rotate in shape, average of 2.5 mm in length and 2 mm in diameter, surface texture glabrous.
*Sepals*.—5, lanceolate in shape, narrow acuminate apex, base fused and broad cuneate, glabrous and matte on both surfaces, entire margin, average of 2.5 mm in length and 0.5 mm in width, color: immature upper and lower surface; 151C to 151D, mature upper and lower surface; 147D, tinged 153D.
*Petals*.—5, rotate with 5 lobes with lower 50% of petal is fused into tube making a campanulate shape, both surfaces are matte and glabrous with only the lower lobe having sparse short hairs an average of 1 mm in length and too small to measure with RHS-CC, lobes; narrow oblong in shape, entire margin, obtuse to broad acute apex, average of 1.4 cm in length and 2.5 mm in width, color: upper surface when opening; 2B with lower lobe 3B, lower surface when opening; 1C, upper surface when fully open; 4A with lower lobe 3A, lower surface when fully open; color between 1A and 2B, color of all lobe surfaces fade to a color between N170A and 170B, tube; average of 6 mm in length and 3 mm in width, color matches lobe coloration, suface matt and glabrous.

Reproductive organs:
*Gynoecium*.—Pistil; 1, average of 1.9 cm in length, style; 1.75 cm in length and 144D in color, stigma; club-shaped and 144D in color, ovary; 146D and tinged 172B to 172C in color.
*Androcoecium*.—Stamens; 5, filaments; 145D in color and 1.2 cm in length, anthers; 3.5 mm in length and 11B in color, dorsifixed, pollen is moderate in quantity and 4D in color.
*Fruit and seed*.—No fruit or seed has been oberved to date.

It is claimed:

1. A new and distinct cultivar of *Diervilla* plant named 'Diwibru01' as herein illustrated and described.

* * * * *